United States Patent [19]

Wilkerson

[11] Patent Number: 5,124,334
[45] Date of Patent: Jun. 23, 1992

[54] BENZYLALCOHOL PHOSPHOLIPASE A$_2$ INHIBITORS

[75] Inventor: Wendell W. Wilkerson, New Castle, Del.

[73] Assignee: Du Pont Merck Pharmaceutical Company, Wilmington, Del.

[21] Appl. No.: 387,319

[22] Filed: Jul. 28, 1989

Related U.S. Application Data

[63] Continuation-in-part of Ser. No. 126,617, Nov. 30, 1987, abandoned.

[51] Int. Cl.$^5$ .................... C07C 211/00; A01N 43/54
[52] U.S. Cl. ................................. 514/277; 514/345; 514/352; 514/357; 514/653; 514/717; 514/718; 514/719; 514/721; 514/825; 514/826; 514/863; 514/886; 546/285; 546/301; 546/304; 546/312; 546/334; 546/339; 564/336; 564/341; 564/355; 564/363; 564/365; 568/583

[58] Field of Search ............... 564/427, 355, 364, 368, 564/387, 336, 341, 363, 365; 568/583; 546/285, 301, 304, 312, 334, 339; 514/653, 717, 718, 719, 721, 345, 352, 357, 277, 886, 825, 826, 863

[56] References Cited

PUBLICATIONS

*Journal of Indian Chemical Society*, vol. 52, No. 9, pp. 875–876, 1975 "Synthesis of New Potential Antispasmodics-antihistamincs".

*Primary Examiner*—C. Warren Ivy
*Assistant Examiner*—Raymond Covington

[57] ABSTRACT

The invention relates to benylalcohol phospholipase A$_2$ inhibitors, pharmaceutical compositions containing them, and methods of treating phospholipase A$_2$-mediated conditions in mammals by administration of a therapeutically effective amount of such a benzylalcohol phospholipase A$_2$ inhibitor.

32 Claims, No Drawings

BENZYLALCOHOL PHOSPHOLIPASE A₂ INHIBITORS

This is a continuation-in-part of application Ser. No. 07/126,617 filed Nov. 30, 1987 now abandoned.

BACKGROUND OF THE INVENTION

This invention relates to benzylalcohols and processes for their preparation, pharmaceutical compositions containing them and pharmaceutical methods using them. These compounds have shown activity as inhibitors of the enzyme phospholipase $A_2$.

The important role of phospholipase $A_2$ in the biosynthesis of prostaglandins and leukotrienes indicates that inhibitors of phospholipase $A_2$ may be valuable therapeutic agents having wide applicability in inflammatory and/or allergic conditions in mammals. Although some currently available anti-inflammatory agents show activity against phospholipase $A_2$ or other enzymes of the "arachidonic acid cascade", there is a continuing need for safer and more effective drugs capable of treating inflammatory and/or allergic diseases.

U.S. Pat. No. 4,239,780 (issued to D. P. Wallach on Dec. 16, 1980) discloses the use for treating phospholipase $A_2$ mediated conditions of compounds of the formula:

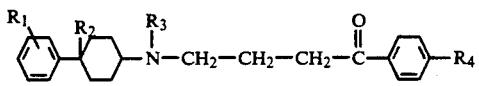

wherein
$R_1$ is 4-Cl, 4-CF$_3$, H, or 2- or 4-CH$_3$;
$R_2$ is CH$_3$—O—, —CH$_2$—OH, or H;
$R_3$ is H or CH$_3$; and
$R_4$ is F or Cl.

These compounds and their activities as inhibitors of phospholipase $A_2$ are also described in D. P. Wallach and V. J. R. Brown, *Biochemical Pharmacology*, 30, 1315 (1981).

SUMMARY OF THE INVENTION

Compounds of Formula I and their pharmaceutically acceptable salts are phospholipase $A_2$ (PLA$_2$) inhibitors and are useful in treating inflammation and other phospholipase $A_2$-mediated conditions in mammals.

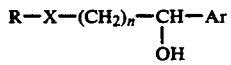   I where
Ar is

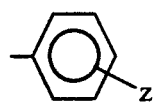

and Z is H, F, Cl, Br, OR¹, or S(O)$_m$R¹ where R¹ is H, methyl, or ethyl, and
m is 0, 1, or 2;
n is 2 or 3;
X is NH or O; and
R is C$_7$–C$_{25}$ alkyl, pyridyl, or mono- or polycyclic benzoid aromatic systems such as

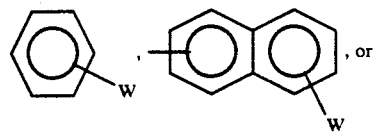

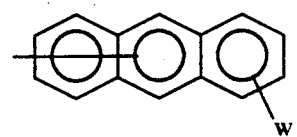

where
W is C$_{1-20}$ alkyl, F, Cl, Br, —OR², —S(O)$_q$R², or perfluoropropanol, or phenyl, and
R² is methyl or ethyl, and
q is 1, 2, or 3; or
R is benzhydryl, phenyl-(4-pyridyl)methyl, C$_7$–C$_{25}$ alkaryl or substituted alkaryl where the substitution is on the aromatic moiety, and is F, Cl, Br, OR³, S(O)$_r$R³, or C$_{1-10}$ alkyl,
where R³ is methyl or ethyl, and r is 0, 1, or 2; provided that when X is O, n must be 3.

Preferred, for reasons of high activity and/or ease of synthesis are those compounds of Formula I described above and their pharmaceutically acceptable salts where
Ar is

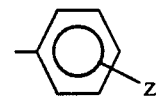

and Z is H, F, Cl, Br, —OCH$_3$, or S(O)$_m$CH$_3$ where m is 0, 1, or 2; and X is NH;

The more preferred compounds of this invention are the compounds of Formula I described above and their pharmaceutically acceptable salts where
Ar is

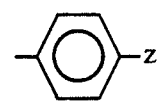

where
Z is H, F, Cl, OCH$_3$, or SCH$_3$;
X is NH; and
R is C$_{10-12}$ alkyl, or

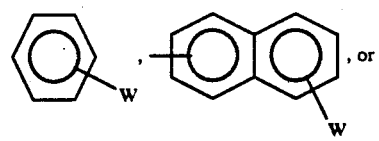

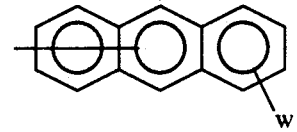

where W is $C_{1-12}$ alkyl; or R is $C_7$-$C_{25}$ alkaryl or substituted alkaryl
where the substitution is on the aryl moiety and is $OCH_3$, $SCH_3$, F, Cl, or $C_{1-10}$ alkyl.

Specifically preferred compounds of the invention are:

Ex. 1: α-(2-([1,4a-Dimethyl-7-(2-propyl)-1,2,3,4,4a,9,10,10a-octahydro-1-phenanthren-1-yl]methylamino)ethyl)-4-fluorobenzenemethanol Hydrochloride.

Ex. 2: α-(3-([1,4a-Dimethyl-1,2,3,4,4a,9,10,10a-octahydro-7-(2-propyl)-1-phenanthrenyl]methylamino)-propyl)-4-fluorobenzenemethanol Hydrochloride.

Ex. 12: α-(2-([1,4a-Dimethyl-1,2,3,4,4a,9,10,10a-octahydro-7-(2-propyl)-1-phenanthrenyl]methylamino)-ethyl)-4-methoxy-benzenemethanol Hydrochloride.

Ex. 13: α-(2-([1,4a-Dimethyl-1,2,3,4,4a,9,10,10a-octahydro-7-(2-propyl)-1-phenanthrenyl]methylamino)-ethyl)benzenemethanol Hydrochloride.

Ex. 14: α-(2-([1,4a-Dimethyl-1,2,3,4,4a,9,10,10a-octahydro-7-(2-propyl)-1-phenanthrenyl]methylamino)-ethyl)-4-methylmercaptobenzenemethanol Hydrochloride.

Ex. 16: 4-Fluoro-α-[2-(6,6-dimethylbicyclo[3.1.1]-heptan-2-yl-methyl)amino]ethyl-benzenemethanol Hydrochloride.

DETAILED DESCRIPTION OF THE INVENTION

The compounds of this invention have demonstrated pharmacological activity as inhibitors of the enzyme phospholipase $A_2$ ($PLA_2$). Phospholipase $A_2$ acts to release arachidonic acid from phospholipids. Once released, arachidonic acid is rapidly metabolized by a variety of enzymes of the "arachidonic acid cascade." The products of the arachidonic acid cascade include prostaglandins, leukotrienes, and related compounds. These compounds exhibit a remarkably broad spectrum of biological activity, and inhibition of their biosynthesis is recognized as a valuable mechanism for production of anti-inflammatory effects.

Both prostaglandins and leukotrienes are believed to have important functions as mediators of inflammation and currently available drugs which inhibit their production are of significant therapeutic value in man and other mammals. Nonsteroidal anti-inflammatory agents such as the salicylates act as inhibitors of prostaglandin synthesis from arachidonic acid by inhibiting the cyclooxygenases. This inhibition of prostaglandin synthesis is believed to be the basis for many of the therapeutic effects of the aspirin-like drugs. The anti-inflammatory activity of the glucocorticosteriods, on the other hand, is believed to be at least partly due to their ability to induce the biosynthesis of a phospholipase $A_2$ inhibitor protein, thereby diminishing the release of arachidonic acid from phospholipids. By decreasing concentrations of arachidonic acid, the substrate for the entire arachidonic acid cascade, production of leukotrienes as well as prostaglandins can be decreased.

Many diseases and conditions in man and other mammals have inflammatory and/or allergic components believed to be mediated by phospholipase $A_2$, e.g., rheumatoid arthritis and other rheumatic disorders, various collagen diseases, dermatoses, psoriasis, hypersensitivity and immune reactions, bronchospastic diseases such as asthma, and disorders of platelet aggregation. Because the compounds of this invention have shown activity as $PLA_2$ inhibitors, valuable pharmacological activity in these and other diseases or conditions mediated by the various products of the arachidonic acid cascade is to be expected.

SYNTHESIS

The compounds of this invention as shown by Formula I, can be prepared by reducing the corresponding ketone with borane-tetrahydrofuran complex ($BH_3$.THF), sodium borohydride, or catalytic hydrogenation as illustrated in Equation 1.

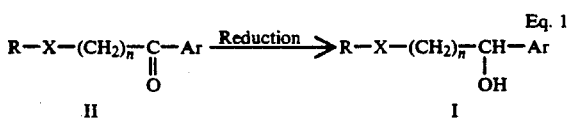

The ketone (II) can be prepared by alkylating an amine (X=NH) or alcohol (X=O) with a haloalkylphenone or its ketal, or an α,β-unsaturated ketone as shown in Equation 2.

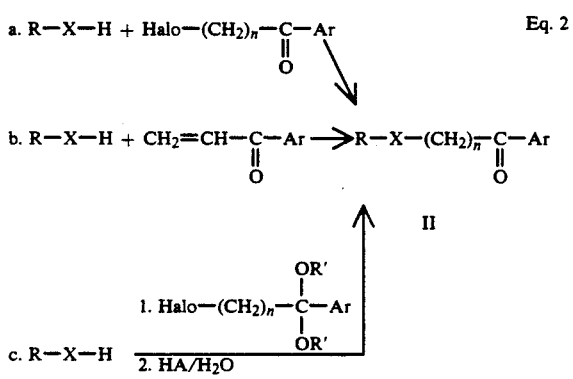

Alternatively, when n=2, the ketone (II) can be prepared by employing the Mannich Reaction described by F. F. Blicke, Organic Reactions, 1(10), 303 (1942), as illustrated in Equation 3.

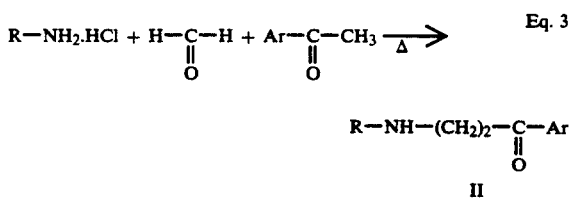

When n is 3, compounds of Formula I can be prepared by reacting an aromatic species with succinic anhydride under Friedel-Craft conditions to give a 3-benzoylpropionic acid. The carboxyl of the keto-acid can be activated by conversion to an active ester, or by conversion to the acid chloride. The resulting activated carboxyl is then allowed to react with an appropriate amine (R—$NH_2$) in an appropriate solvent to afford the keto-amide. The keto-amine can then be reduced to the amino-alcohol by reducing agents such as but not limited to borane or lithium aluminum hydride. This approach is illustrated in Equation 4.

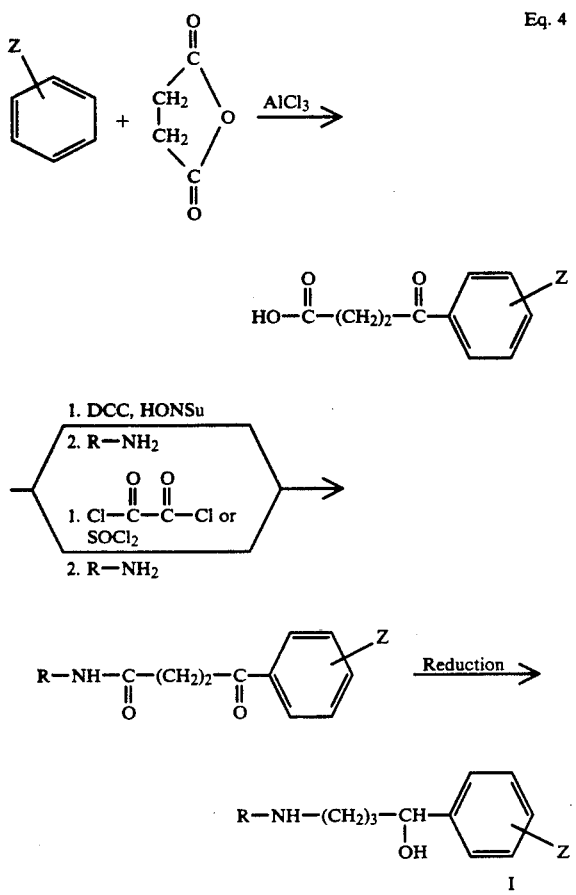

The compounds of the invention may exist, when X is NH, as "free bases", or as pharmaceutically acceptable salts of such acids as hydrochloric acid, hydrobromic acid, sulfuric acid, phosphoric acid, acetic acid, formic acid, citric acid, maleic acid, p-toluenesulfonic acid, or tartaric acid.

The compounds of the invention may also exist as racemic, or where appropriate, diastereomeric mixtures, or the compounds can be resolved into their optically pure isomers by conventional methods such as fractional crystallization of diastereomers or diastereomeric salts, or chromatography.

The compounds of the invention and their syntheses are further illustrated by the following examples. All temperatures are in degrees Celsius. Solvent ratios for thin-layer chromatography (tlc) are by volume.

EXAMPLE 1

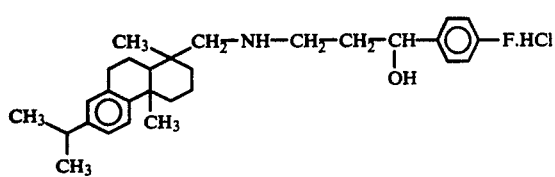

α-(2-[1,4a-Dimethyl-7-(2-propyl)-1,2,3,4,4a,9,10,10a-octahydro-1-phenanthren-1-yl]methylamino)ethyl)-4-fluorobenzenemethanol Hydrochloride A. A solution of 3-chloro-4'-fluoropropiophenone (37.3 g, 0.2 mole) in tetrahydrofuran (100 ml) was treated with triethylamine (22.3 g, 0.22 mole) and stirred at room temperature for one hour. The triethylamine hydrochloride was removed by filtration, and the filtrate was added to a mixture of dehydroabietylamine (57.1 g, 0.2 mole) and p-toluenesulfonic acid monohydrate in tetrahydrofuran (100 ml). The mixture was stirred at reflux for 20 hours and concentrated in vacuo. The residue was triturated with water (400 ml) to give a yellow gum. The aqueous phase was decanted, and the crude product was triturated with diethyl ether (200 ml). The resulting white crystals were collected by filtration, washed with more diethyl ether, and dried to give the aminoketone (58.0 g, 48%); mp 157°–158° C.; IR(nujol) C=O @ 1685 cm$^{-1}$; NMR(DMSO-d$_6$, TMS): δ0.6–2.0(m,24H), 2.27(s,3H,ArCH$_3$), 2.77 (m,1H), 2.87(m,2H,CH$_2$—CO), 3.10(m,1H), 3.50 and 3.73(2m, 4H,CH$_2$—N—CH$_2$), 6.87–8.0(m,11H, aromatic); Anal. Calcd. for C$_{29}$H$_{38}$FNO.C$_7$H$_8$O$_3$S, MW 607.82: C, 71.13; H, 7.63; N, 2.31; S, 5.28. Found: C, 71.10; H, 7.86; N, 2.46; S, 5.46. Mass spectrum m/e 435; $[\alpha]_D^{25}$ +15.8 (c, 1.01, MeOH).

B. The aminoketone of part A (10.0 g, 0.016 mole) was suspended in tetrahydrofuran-isopropanol (75 ml, 2:1), cooled in an ice bath, and treated with sodium borohydride (1.6 g, 0.041 mole). The mixture was allowed to reach room temperature and stirred until no aminoketone was evidenced by tlc (chloroformmethanol, 9:1). The mixture was carefully treated with cold water (50 ml) and stirred for an additional one hour. The mixture was concentrated in vacuo, and the residue was partitioned between methylene chloride (200 ml) and 1N sodium hydroxide (100 ml). The organic layer was washed with water and brine, dried over anhydrous magnesium sulfate, filtered, and concentrated to an oil. The oil was dissolved in diethyl ether and treated with 2N hydrogen chloride-diethyl ether until no further precipitation was observed. The resulting solid was collected by filtration, washed with diethyl ether, and dried to yield the title compound (5.0 g, 64%); mp 194°–202° C.; IR(nujol): OH @ 3344 cm$^{-1}$; Anal. Calcd. for C$_{29}$H$_{40}$FNO.HCl, MW 474.09: C, 73.46; H, 8.72; N, 2.96. Found: C, 73.51; H, 8.82; N, 2.91. Mass spectrum m/e 437,182,164. $[\alpha]_D^{25}$ +26.90° (c, 1.03, MeOH).

EXAMPLE 2

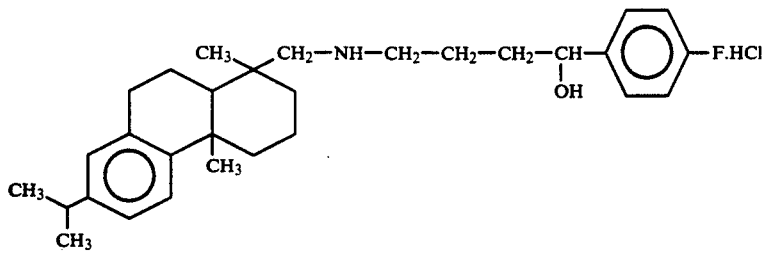

α-(3-([1,4a-Dimethyl-1,2,3,4,4a,9,10,10a-octahydro-7-(2-propyl)-1-phenanthrenyl]methylamino)propyl)-4-fluorobenzenemethanol Hydrochloride A mixture of 4-chloro-4'-fluorobutyrophenone-2,2-dimethylpropylene ketal (28.7 g, 0.1 mole), dehydroabietylamine (28.5 g, 0.1 mole), potassium carbonate (48 g, 0.35 mole), and potassium iodide (1 g) in DMF (200 ml) was stirred at reflux for 24 hours and concentrated in vacuo. The residue was partitioned between ether (300 ml) and water (200 ml). The organic phase was washed with brine, dried over MgSO$_4$, filtered, and concentrated in vacuo to an oil. The oil was dissolved in MeOH (300 ml) and conc. HCl (50 ml) and stirred until no ketal was evidenced by tlc (CHCl$_3$—MeOH, 9:1). The organic solvent was removed in vacuo, and the aqueous phase was made alkaline (pH 8) with 2N NaOH. The mixture was extracted with CH$_2$Cl$_2$ (300 ml). The organic phase was washed with water and brine, dried over MgSO$_4$, filtered, treated with p-toluenesulfonic acid monohydrate, and concentrated in vacuo. The residue was triturated with ether (400 ml) and the resulting solid was collected by filtration, washed with ether, and dried to give the aminoketone (43.3 g, 70%); mp 166°-167° C.; IR(nujol): C=O@ 1687 cm$^{-1}$; NMR(CDCl$_3$,TMS): 35 aliphatic protons and 11 aromatic protons; Anal. Calcd. for C$_{30}$H$_{40}$FNO.C$_7$H$_8$O$_3$S, MW 621.85: C,71.46; H,7.78; N,2.25; S,5.16. Found: C,71.63; H,7.93; N,2.18; S,5.23. Mass spectrum (FAB) m/e 450 (M+1); [α]$_D^{25}$ +20.3° (c,1.05,MeOH).

B. A suspension of the aminoketone of part A (10.0 g, 0.016 mole) in tetrahydrofuran/isopropanol (75 ml, 2:1) was cooled in an ice bath and treated with sodium borohydride (1.2 g, 0.032 mole) and stirred at room temperature until no ketone was evidenced by tlc (chloroform/methanol, 9:1). The mixture was concentrated in vacuo, and the residue was partitioned between diethyl ether (150 ml) and 1N sodium hydroxide (100 ml). The organic phase was washed with water and brine, dried over anhydrous magnesium sulfate, and filtered. The ether filtrate was treated with 1N hydrogen chloride in ether (35 ml), stirred, and placed in the cold for 24 hours. The resulting solid was collected by filtration, washed with ether, and dried to give the title compound (6.0 g, 76%); mp 195°-198° C.; IR(nujol): OH@ 3348 cm$^{-1}$; Anal. Calcd. for C$_{30}$H$_{42}$FNO.HCl, MW 488.11: C, 73.81; H, 8.88; N, 2.87. Found: C, 73.62; H, 8.96; N, 2.68. Mass spectrum m/e 451,368. [α]$_D^{25}$ +15.8 (c,1.01,MeOH).

EXAMPLE 3

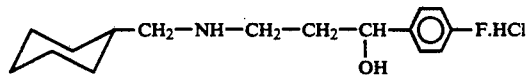

α-[2-(cyclohexanemethylamino)ethyl-4-fluorobenzenemethanol Hydrochloride

A. A solution of cyclohexanemethylamine (22.6 g, 0.2 mole) in ethanol (100 ml) was cooled in an ice bath and treated dropwise with a solution of 3-chloro-4'-fluoropropiophenone (37.3 g, 0.2 mole) in tetrahydrofuran (100 ml). The mixture was stirred for three hours in the ice bath followed by 24 hours at room temperature. The resulting crystals were collected by filtration, washed with diethyl ether and dried to give a pure aminoketone (31.8 g, 53%) product; mp 181°-183° C.; IR(nujol): C=O@ 1690 cm$^{-1}$; NMR(CDCl$_3$, TMS): δ0.87-2.1(2m, 11H, cyclohexyl), 2.87(t,2H,CH$_2$CO), 3.43(t,2H, N-CH$_2$), 3.76(t,2H,N-CH$_2$), [7.10(d of d,2H) and 8.0(m,2H) p-F-phenyl]; mass spectrum m/e 263.

B. A suspension of the aminoketone from part A (40.0 g, 0.133 mole) in tetrahydrofuran (150 ml) and isopropanol (50 ml) was cooled in an ice bath and treated in small portions with sodium borohydride (5.05 g, 0.133 mole). The mixture was stirred in the ice bath for two hours followed by 16 hours at room temperature. The mixture was treated with water (50 ml) and concentrated in vacuo. The residue was treated with 2N hydrochloric acid (100 ml) and triturated. The resulting solid was collected by filtration, washed with water and diethyl ether, and dried to give the title compound (40.0 g 99%); mp 179°-180° C.; IR(nujol): OH@ 3360 cm$^{-1}$; NMR(DMSO-d$_6$, TMS): δ0.67-1.83(m, 11H, cyclohexyl), 1.97(m,2H,CH$_2$), 2.68(t,2H,N—CH$_2$), 2.90(t,2H,N—CH$_2$), 4.70(t,1H,N—C—H), 5.63(s,1H,OH), [7.13 (d of d,2H) and 7.37(m,2H) p-F-phenyl]; Anal. Calcd. for C$_{16}$H$_{24}$FNO.HCl, MW 301.83: C, 63.66; H, 8.35; N, 4.64. Found: C,63.60; H,8.35; N,4.50. Mass spectrum m/e 265.

EXAMPLE 4

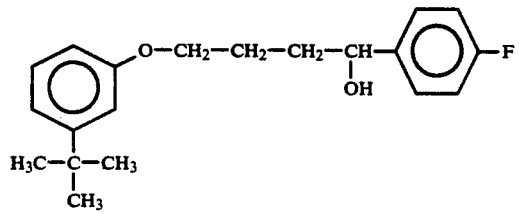

4-Fluoro-α-[3-(2-methyl-2-propyl)phenoxy]propylbenzenemethanol

A. A suspension of sodium hydride (2.6 g, 0.11 mole) and 4-chloro-4'-fluorobutyrophenone-2,2-dimethyl-propylene ketal (28.7 g, 0.1 mole) in dry N,N-dimethylformamide (100 ml) was cooled in an ice bath with stirring and treated dropwise over one hour with a solution of 3-tert-butylphenol (15.0 g, 0.1 mole) in dry N,N-dimethylformamide (75 ml). The mixture was removed from the ice bath, stirred at room temperature for four hours, and then at reflux for 16 hours. The mixture was concentrated in vacuo, and the residue was partitioned between diethyl ether (200 ml) and saturated sodium bicarbonate (100 ml). The organic phase was washed with bicarbonate, water, and brine; dried over anhydrous magnesium sulfate; filtered; and concentrated to an oily ketal (40.0 g, 100%). The IR(neat) showed no OH or C=O. The ketal (33.0 g, 0.082 mole) was dissolved in methanol (100 ml), treated with concentrated hydrochloric acid (25 ml), and stirred at room temperature until no ketal was evidenced by tlc (chloroform/methanol, 9:1). The mixture was diluted to 500 ml with water, and the resulting solid was collected by filtration, washed with water, and dried to give the phenoxy ketone (25 g, 97%) after recrystallization from cold ethanol; mp 69°-70° C.; IR(nujol): C=O@ 1678 cm$^{-1}$; NMR(CDCl$_3$, TMS): δ1.33(s,9H,tBu), 2.25(d of t,2H,CH$_2$), 3.20(t,2H,CH$_2$CO), 4.08(t,2H,O—CH$_2$), [6.73(m,1H), 6.8-7.3(m,5H), 8.00(m,2H) aromatics]; Anal. Calcd. for C$_{20}$H$_{23}$FO$_2$, MW 314.38: C, 76.40; H, 7.37. Found: C, 76.43; H, 7.30. Mass spectrum m/e 314.

B. The phenoxy ketone of part A (6.0 g, 0.019 mole) in dry tetrahydrofuran (50 ml) was cooled in an ice bath and treated with 1M borane-tetrahydrofuran complex (25 ml, 0.025 mole) and stirred at room temperature for four hours. The mixture was cooled in an ice bath, and the excess borane was decomposed with water. The mixture was concentrated in vacuo, and the residue was triturated with concentrated hydrochloric acid (50 ml) at 80° C. for one hour. The aqueous mixture was extracted with diethyl ether (100 ml). The ether extract was washed with water and brine, dried over anhydrous magnesium sulfate, filtered, and concentrated to an oil 5.5 g (91%: IR(neat): OH@ 3392 cm$^{-1}$; NMR(CDCl$_3$, TMS): δ1.30(s,9H,tBu), 1.6-2.0(m,4-H,O—C—CH$_2$—CH$_2$), 3.98(t,2H,O—CH$_2$), 4.73(t,1H,H—C—O), 6.5-7.4(m,8H,aromatic); mass spectrum m/e 316.

EXAMPLE 5

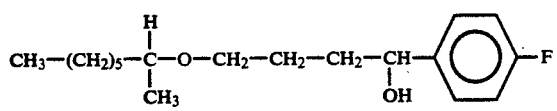

4-Fluoro-α-[3-(2-octyloxy)propyl]benzenemethanol

By substituting d-octanol in Example 4, the title compound was obtained as a mixture of diastereomers in 91% yield as an oil; IR(neat): OH@ 3412 cm$^{-1}$; NMR: δ0.88(t,3h,CH$_3$), 1.15(d,3H, O—C—CH$_3$), 1.28(m,8H,C$_4$H$_8$), 1.5-1.9(m,4H,2 O—C—CH$_2$), 3.2-3.6(m,3H, O—CH$_2$+O—CH), 6.7-7.4(m,4-H,aromatic); mass spectrum m/e 296.

EXAMPLE 6

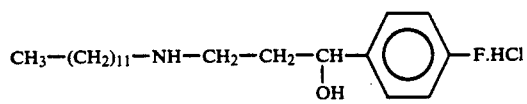

α-(2-Dodecylamino-ethyl)-4-fluorobenzenemethanol Hydrochloride

The title compound was prepared as described in Example 1 in 55% yield from the corresponding ketone; mp 235° C. dec.

EXAMPLE 7

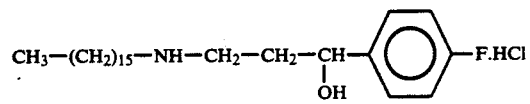

α-(2-(Hexadecylamino-ethyl)-4-fluorobenzenemethanol Hydrochloride

The title compound was prepared as described in Example 1 in 74% yield from the corresponding ketone; mp 210° C. dec.

EXAMPLE 8

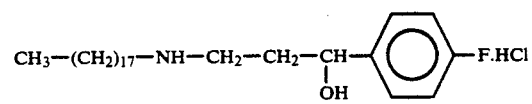

4-Fluoro-α-(2-octadecylamino-ethyl)benzenemethanol Hydrochloride

The title compound was prepared as described in Example 1 in 53% yield; mp 233°-234° C.

EXAMPLE 9

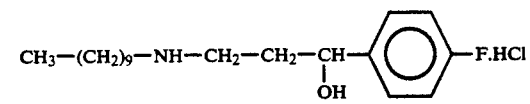

α-(2-Decylamino-ethyl)-4-fluorobenzenemethanol Hydrochloride

The title compound was prepared as described in Example 1 in 32% yield; mp 163°-165° C.

EXAMPLE 10

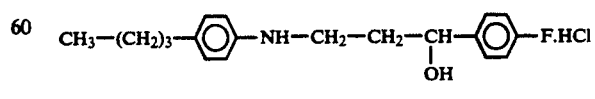

α-[2-(4-Butylphenyl)amino-ethyl]-4-fluorobenzenemethanol Hydrochloride

The title compound was prepared according to the procedure in Example 3 in 80% yield; mp 163°-164° C.

EXAMPLE 11

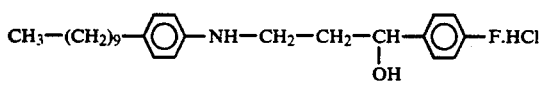

α-[2-(4-Decylphenyl)amino-ethyl]-4-fluorobenzenemethanol Hydrochloride

The title compound was prepared as described in Example 3 in 100% yield; mp 175° C. dec.

EXAMPLE 12

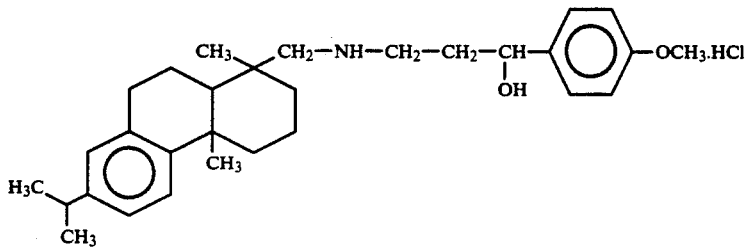

α-(2-([1,4a-Dimethyl-1,2,3,4,4a,9,10,10a-octahydro-7-(2-propyl)-1-phenanthrenyl]methylamino)-ethyl)-4-methoxybenzenemethanol Hydrochloride The title compound was prepared as described in Example 1 in 88% yield; mp 135°-137° C.

EXAMPLE 13

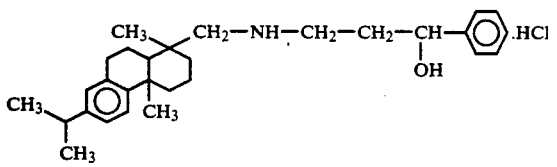

α-(2-([1,4a-Dimethyl-1,2,3,4,4a,9,10,10a-octahydro-7-(2-propyl)-1-phenanthrenyl]methylamino)ethyl)benzene-methanol Hydrochloride The title compound was prepared as described in Example 1 in 50% yield; mp 130°-132° C.

EXAMPLE 14

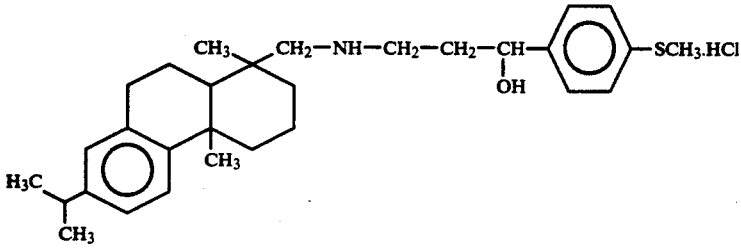

α-(2-([1,4a-Dimethyl-1,2,3,4,4a,9,10,10a-octahydro-7-(2-propyl)-1-phenanthrenyl]methylamino)ethyl)-4-methylmercaptobenzenemethanol Hydrochloride The title compound was prepared as described in Example 1 in 75% yield; mp 158° C. dec.

EXAMPLE 15

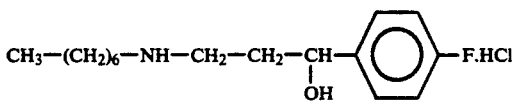

4-Fluoro-α-(2-heptylaminoethyl)-benzenemethanol Hydrochloride

The title compound was prepared as described in Example 1 in 91% yield; mp 165°-167° C.

EXAMPLE 16

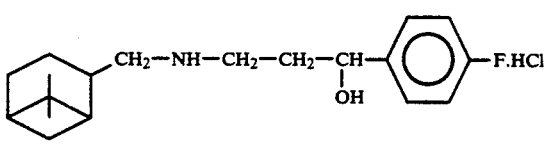

4-Fluoro-α-[2-(6,6-dimethylbicyclo[3.1.1]heptan-2-yl-methyl)amino]ethyl-benzenemethanol Hydrochloride The title compound was prepared as described in Example 3 in 40% yield after fractional crystallization from ethanol/diethyl ether; mp 195°-198° C.; IR(nujol)-

:OH@ 3340 cm$^{-1}$; [α]$_D^{25}$ −20.1° (c, 1.02, MeOH); mass spectrum m/e 305.

EXAMPLE 17

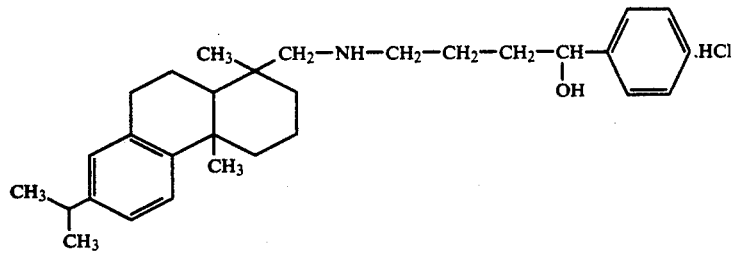

1-Phenyl-{[1,4A-dimethyl-7-(1-methylethyl)-1,2,3,4,4A, 9,10,10A-octahydro-1-phenanthren-1-yl]-methylamino}-1-butanol Hydrochloride.

A1. A mixture of 3-benzoylpropionic acid (17.8 g, 0.1 mole) in 100 ml methylene chloride was cooled in an ice bath and treated dropwise with oxalyl chloride (14.0 g, 0.11 mole). After the addition of the oxalyl chloride, the ice bath was removed and the mixture was stirred at room temperature until no acid was evidenced by IR spectroscopy. The mixture was concentrated in vacuo at 50° C. The residue was dissolved in 100 ml methylene chloride and treated dropwise with a solution of dehydroabietylamine (28.5 g, 0.1 mole) and triethylamine (10.1 g, 0.1 mole) in 100 ml methylene chloride. The reaction mixture was stirred at room temperature for 24 hours and concentrated in vacuo. The residue was partitioned between 300 ml ethyl acetate and 200 ml 1N hydrochloric acid. The organic layer was washed with water and brine, dried over anhydrous magnesium sulfate, filtered and concentrated to an homogeneous (tlc, chloroform-methanol, 9:1) red oil in 100% yield (45.0 g); IR(neat): N-H@ 3323 cm$^{-1}$ and C=O@ 1686 and 1656 cm$^{-1}$.

A2. A mixture of 3-benzoylpropionic acid (7.4 g, 0.042 mole) and N-hydroxysuccinimide (NSu) (5.3 g, 0.046 mole) in 100 ml methylene chloride was cooled in an ice bath and treated with N,N'-dicyclohexylcarbodiimide (DCC) (9.4 g, 0.046 mole). The mixture was stirred at room temperature for 24 hours. The resulting dicyclohexylurea was removed by filtration, and the filtrate was concentrated in vacuo. The residue was dissolved in 100 ml tetrahydrofuran, treated with dehydroabietylamine (12.0 g, 0.042 mole) and 100 ml saturated sodium bicarbonate. The reaction mixture was stirred at room temperature of 24 hours, and the organic solvent was removed in vacuo. The aqueous phase was partitioned between 200 ml ethyl acetate and 100 ml 5% sodium bicarbonate. The organic layer was washed with water. 1N hydrochloric acid, water, and brine; dried over anhydrous magnesium sulfate; filtered; and concentrated to an oil in 100% yield (18.5 g); IR(neat): N-H@ 3320 cm$^{-1}$; C=O@ 1685 and 1651 cm$^{-1}$; NMR (CDCl$_3$, TMS): δ0.6-2.0(m, 21H), 2.27("d", 1H, Ar-C-H), 2.63(t, 2H, O=C-CH$_2$), 2.88(m, 2H, Ar-CH$_2$), 3.20(m, 2H, N-CO-CH$_2$), 3.37(t, 2H, N-CH$_2$), 5.90(s, 1H, N-H), 6.8-8.05(m, 8H, aromatic); Anal. Calcd. for C$_{30}$H$_{39}$NO$_2$, MW 445.62: C, 80.85; H, 8.82; N, 3.14. Found: C, 80.63; H, 8.99; N, 3.42. Mass spectrum m/e 446. (M+1); [α]$_D^{25}$ +24.27° (c, 1, MeOH).

B. A solution of the keto-amide from part A (22.0 g, 0.049 mole) in 50 ml dry tetrahydrofuran was treated dropwise with 1M lithium aluminum hydride (LAH) (150 ml, 600 meq) and refluxed for 24 hours. The excess LAH was decomposed with water and 15% sodium hydroxide. The mixture was diluted with 200 ml tetrahydrofuran and filtered through Celite. The filtrate was concentrated in vacuo, and the residue was partitioned between 200 ml methylene chloride and 100 ml 1N sodium hydroxide. The organic layer was washed with water and brine, dried over anhydrous magnesium sulfate, filtered, and concentrated to an oil. The oil was allowed to react with excess 3N hydrogen chloride/diethyl ether to give a gummy material which was crystallized from hot acetonitrile to give the product in 57% yield (13.1 g); mp 205°-207° C.; IR(nujol): OH@ 3352 cm$^{-1}$; NMR (DMSO-d$_6$, TMS) δ0.6-2.0 (m, 25H), 2.27 ("d", 1H, Ar-C-H), 2.85(m, 6H, CH$_2$-N-CH$_2$ and Ar-CH$_2$), 4.57 (m, 1H, O-C-H), 5.40(d, 1H, OH), 6.8-7.4(m, 8H, aromatic), 8.40 (s, 2H, H$_2$N Cl). Anal. Calcd. for C$_{30}$H$_{43}$NO.HCl, MW 470.12: C, 76.64; H, 9.43; N, 2.98. Found: C, 76.60; H, 9.50; N, 2.90. Mass spectrum m/e 434(M+1); [α]$_D^{25}$ +12.90° (c, 1, MeOH).

When the reduction was carried out with borane-tetrahydrofuran complex, the identical product was obtained.

The compounds prepared according to the procedures illustrated in Examples 1 to 16 are listed in Table I.

Dehydroabietyl refers to the group 1,4a-dimethyl-7-(2-propyl)-1,2,3,4,4a, 9,10,10a-octahydro-1-phenanthren-1-yl-methyl. Myrtanyl refers to the group 6,6-dimethylbicyclo[3.1.1.]heptan-2-yl-methyl.

TABLE I

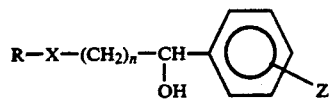

| Ex. | R | X | n | Z | mp °C. | Yield % |
|---|---|---|---|---|---|---|
| 1 | DEHYDROABIETYL | NH | 2 | p-F | 194-202 | 64 |
| 2 | DEHYDROABIETYL | NH | 3 | p-F | 195-198 | 76 |
| 3 | CYCLOHEXANEMETHYL | NH | 2 | p-F | 179-180 | 99 |
| 4 | 3-t-BUTYLPHENYL | O | 3 | p-F | OIL | 91 |
| 5 | d-2-OCTYL | O | 3 | p-F | OIL | 91 |
| 6 | n-DODECYL | NH | 2 | p-F | 235 dec. | 55 |
| 7 | n-HEXADECYL | NH | 2 | p-F | 210 dec. | 74 |
| 8 | n-OCTADECYL | NH | 2 | p-F | 233-234 | 53 |
| 9 | n-DECYL | NH | 2 | p-F | 163-165 | 32 |
| 10 | 4-n-BUTYL- | NH | 2 | p-F | 163-164 | 80 |

TABLE I-continued $$R-X-(CH_2)_n-\underset{OH}{CH}-C_6H_4-Z$$

| Ex. | R | X | n | Z | mp °C. | Yield % |
|---|---|---|---|---|---|---|
| 11 | 4-n-DECYL-PHENYL | NH | 2 | p-F | 175 dec | 100 |
| 12 | DEHYDRO-ABIETYL | NH | 2 | p-OCH$_3$ | 135–137 | 88 |
| 13 | DEHYDRO-ABIETYL | NH | 2 | H | 130–132 | 50 |
| 14 | DEHYDRO-ABIETYL | NH | 2 | p-SCH$_3$ | 158 dec. | 75 |
| 15 | n-HEPTYL | NH | 2 | p-F | 165–167 | 91 |
| 16 | cis-MYRTANYL | NH | 2 | p-F | 195–198 | 40 |
| 17 | Dehydroabietyl | NH | 3 | H | 205–207 | 57 |

By using the methods described in the preceding examples, other compounds of Formula I can be prepared. Examples of such compounds are listed in Table II.

TABLE II $$R-X-(CH_2)_n-\underset{}{\overset{OH}{CH}}-C_6H_4-Z$$

| Ex. | R | X | n | Z |
|---|---|---|---|---|
| 18 | CH$_3$—(CH$_2$)$_{11}$—C$_6$H$_4$— | O | 3 | p-F |
| 19 | 2-naphthyl-CH$_2$—CH$_2$ | O | 3 | p-SCH$_3$ |
| 20 | myrtanyl-CH$_2$ | O | 3 | p-F |
| 21 | myrtanyl-CH$_2$ | O | 3 | p-SCH$_3$ |
| 22 | myrtanyl-CH$_2$ | O | 3 | p-Br |
| 23 | myrtanyl-CH$_2$ | NH | 3 | p-F |
| 24 | myrtanyl-CH$_2$ | NH | 3 | p-SO$_2$CH$_3$ |
| 25 | 6-(CH$_3$—(CH$_2$)$_7$)-2-naphthyl-CH$_2$—CH$_2$ | NH | 2 | p-F |
| 26 | 6-(CH$_3$—(CH$_2$)$_7$)-2-naphthyl-CH$_2$—CH$_2$ | NH | 3 | p-F |

TABLE II-continued $$R-X-(CH_2)_n-\overset{OH}{\underset{|}{CH}}-\text{C}_6H_4-Z$$

| Ex. | R | X | n | Z |
|---|---|---|---|---|
| 27 | CH₃—(CH₂)₉—(naphthalene)—CH₂—CH₂— | NH | 3 | p-F |
| 28 | (naphthalene)—CH₂—CH₂— | NH | 3 | p-Br |
| 29 | CF₃—(phenyl)—(cyclohexyl)— | NH | 3 | p-F |
| 30 | CF₃—(phenyl)—(cyclohexyl)— | NH | 3 | p-OCH₃ |
| 31 | CF₃—(phenyl)—(cyclohexyl)— | NH | 3 | H |
| 32 | CF₃—(phenyl)—(cyclohexyl)— | NH | 2 | p-SCH₃ |
| 33 | Cl—(phenyl)—(cyclohexyl)— | NH | 2 | p-F |
| 34 | (pyridyl)(phenyl)CH— | NH | 3 | p-F |
| 35 | (pyridyl)(phenyl)CH— | O | 3 | p-F |
| 36 | CH₃—(CH₂)₁₁—(phenyl)— | NH | 3 | p-F |
| 37 | HO—C(CF₃)₂—(phenyl)— | NH | 3 | p-F |

TABLE II-continued $$R-X-(CH_2)_n-\underset{\underset{OH}{|}}{CH}-\text{C}_6\text{H}_4-Z$$

| Ex. | R | X | n | Z |
|---|---|---|---|---|
| 38 | HO-C(CF$_3$)$_2$-C$_6$H$_4$- | NH | 3 | p-SCH$_3$ |
| 39 | cyclohexyl-CH$_2$- | NH | 3 | p-SCH$_3$ |
| 40 | CH$_3$-C$_6$H$_4$-C$_6$H$_4$-CH$_2$- | NH | 3 | p-F |
| 41 | anthracenyl-CH$_2$- | NH | 2 | p-Cl |
| 42 | anthracenyl-CH$_2$- | NH | 3 | p-F |
| 43 | (abietyl)-CH$_2$- | NH | 3 | p-OCH$_3$ |
| 44 | (dehydroabietyl)-CH$_2$ | NH | 2 | p-SCH$_3$ |
| 45 | (dehydroabietyl)-CH$_2$ | O | 3 | H |
| 46 | (abietyl)-CH$_2$- | NH | 3 | p-F |
| 47 | DEHYDROABIETYL | NH | 2 | o-Cl |

TABLE II-continued

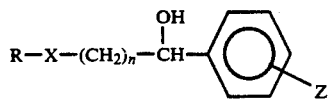

| Ex. | R | X | n | Z |
|---|---|---|---|---|
| 48 | (naphthylethyl) CH₂—CH₂ | NH | 3 | m-Cl |
| 49 | DEHYDROABIETYL | NH | 2 | o-Br |
| 50 | (naphthylethyl) CH₂—CH₂ | NH | 3 | m-Br |

DOSAGE AND DOSAGE FORMS

The phospholipase $A_2$ inhibitors of this invention can be administered to treat inflammatory and/or allergic conditions, including but not limited to rheumatoid arthritis, and other rheumatic disorders, collagen diseases, dermatoses, allergic diseases, chronic obstructive and bronchospastic lung diseases such as asthma and bronchitis. The compounds of this invention may also be useful in the treatment of osteoarthritis.

They may be administered by any means that enables the active agent to reach the agent's site of action in the body of a mammal. They can be administered by any conventional means available for administration of pharmaceuticals, either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, and, if necessary, suitable stabilizing agents, and/or, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

SOFT GELATIN CAPSULES

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

NASAL SPRAY

An aqueous solution is prepared such that each 1 milliliter contains 10 milligrams of active ingredient, 1.8 milligrams methylparaben, 0.2 milligrams propylparaben and 10 milligrams methylcellulose. The solution is dispensed into 1 milliliter vials.

LUNG INHALER

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

TOPICAL FORMULATION

An ointment for topical administration may be prepared by adding the active ingredient to a mixture of 48% by weight white petrolatum, 10% liquid petrolatum, 8% glycerol monostearate, 3% isopropyl myristate and 20% lanolin at 70° C. After thorough mixing, a warm solution of methyl and propyl parabens in water containing sodium acetone bisulfite is added such that the final concentration of each paraben is 0.15%, of water is 8% and of sodium acetone bisulfite is 0.5%. The mixture is stirred until it has reached room temperature.

PHOSPHOLIPASE $A_2$ INHIBITION TEST SYSTEM

The compounds of this invention have been shown to inhibit phospholipase $A_2$ in an in vitro test system using the porcine pancreatic $PLA_2$ enzyme and an assay modified from Hirata et al. (*Proc. Natl. Acad. Sci (USA)*, 77, 2533, 1980). The reaction was run in a total volume of 0.1 ml with the enzyme at a final concentration of 19 units/ml (0.025 μg protein/ml) which gave approximately 5000–8000 dpm (disintegration per minute) of activity in a buffer containing 25 mM Tris (trihydroxymethyl aminoethane), 25 mM glycylglycine, 25 mM $CaCl_2$ and 0.75 mM EDTA (tetra sodium salt), pH 8.5. The drug was added to the enzyme solution, incubated for 2 minutes, and the substrate, [arachidonyl-1-$^{14}$C] L-α-1-palmitoyl-2-arachidonyl phosphatidylcholine, at a final concentration of 7 μM (40,000 dpm), was then added to begin the reaction which proceeded for five minutes at 37° C. The reaction was stopped by freezing in a dry ice-ethanol slurry and the arachidonic acid products were separated from the unreacted substrate using silica gel columns.

All reactions were run in duplicate. Inhibitors were dissolved in 0.2M Tris-Cl (trihydroxymethyl aminoethane hydrochloride), pH 8.5 or dissolved in DMSO and then diluted with Tris-Cl buffer (maximum DMSO concentration, 7%). The $IC_{50}$ value was determined by inspection of a semilog plot of percent inhibition versus final inhibitor concentration.

The enzyme phospholipase $A_2$ ($PLA_2$), catalyzes the release of fatty acids from the 2-position of phospholipids, particularly phosphatidyl choline. Arachidonic acid (AA) is most frequently found at the 2-position of phospholipids. Once it is released by the action of $PLA_2$, AA can be oxygenated by cyclooxygenases and lipoxygenases to the potent inflammatory mediators prostaglandins and leukotrienes, respectively. Inhibition of $PLA_2$ will block the generation of these local inflammatory mediators, thereby reducing inflammation. Since AA is the substrate for both cyclooxygenases and lipoxygenases, inhibition of $PLA_2$ will reduce the levels of both prostaglandins and leukotrienes. Many current anti-inflammatory drugs, e.g., salicylates, inhibit cyclooxygenases but not lipoxygenases, so that only prostaglandin levels are reduced.

TPA INFLAMMATION INHIBITION TEST

The compounds of Formula (I) have been shown to be efficacious in murine models of skin inflammatory diseases. One such model is the inflammation induced by tetradecanoyl phorbol acetate (TPA), modified from the method of Kuehl et al., *Nature*, 1977, 265, 170; and Van Arman, *Clin. Pharmacol. Ther.*, 1974, 16, 900. The TPA model mimics many of the inflammatory change which occur in human skin diseases such as psoriasis, since elevated levels of inflammatory arachidonic acid metabolites are found and an influx of polymorphonuclear leukocytes is observed. The test procedure used to evaluate the compounds of Formula (I) is as follows: the test compound (100 mg/ear) is applied to both ears of mice in an appropriate vehicle, such as acetone, and then the inflammatory stimulus (TPA) is applied to the right ear. Four hours later, the edema is measured by removing standard size discs from the ears using a biopsy punch. A control group of animals receives TPA in vehicle applied to the right ear, and vehicle alone to the left ear. The weights of the ear discs are determined, and the suppression of swelling observed in animals treated with the test compound is determined. Results obtained in this model for selected compounds of Formula (I) are shown in Table III.

TABLE III

| Example | % Inhibition of Control Swelling |
|---------|----------------------------------|
| 1       | 46                               |
| 2       | 57                               |
| 12      | 27                               |

"Consisting essentially of" in the present disclosure is intended to have its customary meaning; namely, that all specified materials and conditions are very important in practicing the invention but that unspecified materials and conditions, including other therapeutic agents, are not excluded so long as they do not prevent the benefits of the invention from being realized.

What is claimed is:

1. A substituted benzylalcohol phospholipase A₂ inhibitor of the formula:

$$R-X-(CH_2)_n-\underset{\underset{OH}{|}}{CH}-Ar \qquad (I)$$

or a pharmaceutically acceptable salt thereof, wherein
Ar is

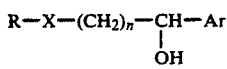

and Z is H, F, Cl, Br, —OR¹, or —S(O)ₘR¹, where R¹ is H, methyl, or ethyl, and m is 0, 1, or 2;
n is 2 or 3;
X is NH or O; and
R is C₇–C₂₅ alkyl, pyridyl, or
R is benzhydryl, phenyl-(4-pyridyl)methyl, C₇–C₂₅ alkaryl or substituted alkaryl where the substitution is on the aromatic moiety and is F, Cl, Br, —OR³, —S(O)ᵣR³, or C₁–C₁₀ alkyl, where
R³ is methyl or ethyl, and r is 0, 1, or 2;
provided that when X is O, n must be 3.

2. A substituted benzylalcohol phospholipase A₂ inhibitor of claim 1, wherein
Ar is

and Z is H, F, Cl, Br, —OCH₃, or —S(O)ₘCH₃, where m is 0, 1, or 2; and
X is NH.

3. A substituted benzylalcohol phospholipase A₂ inhibitor of claim 2, wherein
Ar is

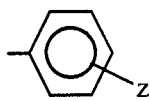

and Z is H, F, Cl, —OCH₃, or —SCH₃;
X is NH; and
R is C₁₀–C₁₂ alkyl,
or R is C₇–C₂₅ alkaryl or substituted alkaryl, where the substitution is on the aryl moiety and is —OCH₃, —SCH₃, F, Cl, or C₁–C₁₀ alkyl.

4. The compound of claim 1 which is α-(2-([1,4a-Dimethyl-7-(2-propyl)-1,2,3,4,4a,9,10,10a-octahydro-1-phenanthren-1-yl]methylamino)ethyl)-4-fluorobenzenemethanol Hydrochloride.

5. The compound of claim 1 which is α-(3-([1,4a-Dimethyl-1,2,3,4,4a,9,10,10a-octahydro-7-(2-propyl)-1-phenanthrenyl]methylamino)-propyl)-4-fluorobenzenemethanol Hydrochloride.

6. The compound of claim 1 which is α-(2-([1,4a-Dimethyl-1,2,3,4,4a,9,10,10a-octahydro-7-(2-propyl)-1-phenanthrenyl]methylamino)-ethyl)-4-methoxy-benzenemethanol Hydrochloride.

7. The compound of claim 1 which is α-(2-([1,4a-Dimethyl-1,2,3,4,4a,9,10,10a-octahydro-7-(2-propyl)-1-phenanthrenyl]methylamino)-ethyl)benzenemethanol Hydrochloride.

8. The compound of claim 1 which is α-(2-([1,4a-Dimethyl-1,2,3,4,4a,9,10,10a-octahydro-7-(2-propyl)-1-phenanthrenyl]methylamino)-ethyl)-4-methylmercaptobenzenemethanol Hydrochloride.

9. The compound of claim 1 which is 4-Fluoro-α-[2-(6,6-dimethylbicyclo[3.1.1]-heptan-2-yl-methyl)amino]ethyl-benzenemethanol Hydrochloride.

10. A pharmaceutical composition, consisting essentially of a substituted benzylalcohol phospholipase A₂ inhibitor of claim 1 in an amount sufficient to provide anti-inflammatory and/or anti-allergic effects in a mammal suffering from a phospholipase A₂-mediated condition, and a pharmaceutically acceptable carrier.

11. A pharmaceutical composition, consisting essentially of a substituted benzylalcohol phospholipase A₂ inhibitor of claim 2 in an amount sufficient to provide anti-inflammatory and/or anti-allergic effects in a mammal suffering from a phospholipase A₂-mediated condition, and a pharmaceutically acceptable carrier.

12. A pharmaceutical composition, consisting essentially of a substituted benzylalcohol phospholipase A₂ inhibitor of claim 3 in an amount sufficient to provide anti-inflammatory and/or anti-allergic effects in a mammal suffering from a phospholipase A₂-mediated condition, and a pharmaceutically acceptable carrier.

13. A pharmaceutical composition according to claim 10 wherein the substituted benzylalcohol phospholipase A₂ inhibitor is α-(2-([1,4a-Dimethyl-7-(2-propyl)-1,2,3,4,4a,9,10,10a-octahydro-1-phenanthren-1-yl]methylamino)ethyl)-4-fluorobenzenemethanol Hydrochloride.

14. A pharmaceutical composition according to claim 10 wherein the substituted benzylalcohol phospholipase A₂ inhibitor is α-(3-([1,4a-Dimethyl-1,2,3,4,4a,9,10,10a-octahydro-7-(2-propyl)-1-phenanthrenyl]methylamino)-propyl)-4-fluorobenzenemethanol Hydrochloride.

15. A pharmaceutical composition according to claim 10 wherein the substituted benzylalcohol phospholipase A₂ inhibitor is α-(2-([1,4a-Dimethyl-1,2,3,4,4a,9,10,10a-octahydro-7-(2-propyl)-1-phenanthrenyl]methylamino)-ethyl)-4-methoxy-benzenemethanol Hydrochloride.

16. A pharmaceutical composition according to claim 10 wherein the substituted benzylalcohol phospholipase A₂ inhibitor is α-(2-([1,4a-Dimethyl-1,2,3,4,4a,9,10,10a-octahydro-7-(2-propyl)-1-phenanthrenyl]methylamino)-ethyl)benzenemethanol Hydrochloride.

17. A pharmaceutical composition according to claim 10 wherein the substituted benzylalcohol phospholipase A₂ inhibitor is α-(2-([1,4a-Dimethyl-1,2,3,4,4a,9,10,10a-octahydro-7-(2-propyl)-1-phenanthrenyl]methylamino)-ethyl)-4-methylmercaptobenzenemethanol Hydrochloride.

18. A pharmaceutical composition according to claim 10 wherein the substituted benzylalcohol phospholipase A₂ inhibitor is 4-Fluoro-α-[2-(6,6-dimethylbicyclo[3.1.1]-heptan-2-yl-methyl)amino]ethyl-benzenemethanol Hydrochloride.

19. A method of treating inflammatory and/or allergic conditions mediated by phospholipase A₂ in a mammal, comprising administering to the mammal a therapeutically effective amount of a phospholipase A₂ inhibitor of claim 1.

20. A method of treating inflammatory and/or allergic conditions mediated by phospholipase $A_2$ in a mammal, comprising administering to the mammal a therapeutically effective amount of a phospholipase $A_2$ inhibitor of claim 2.

21. A method of treating inflammatory and/or allergic conditions mediated by phospholipase $A_2$ in a mammal, comprising administering to the mammal a therapeutically effective amount of a phospholipase $A_2$ inhibitor of claim 3.

22. A method of treating inflammatory and/or allergic conditions mediated by phospholipase $A_2$ in a mammal, comprising administering to the mammal a therapeutically effective amount of the phospholipase $A_2$ inhibitor of claim 4.

23. A method of treating inflammatory and/or allergic conditions mediated by phospholipase $A_2$ in a mammal, comprising administering to the mammal a therapeutically effective amount of the phospholipase $A_2$ inhibitor of claim 5.

24. A method of treating inflammatory and/or allergic conditions mediated by phospholipase $A_2$ in a mammal, comprising administering to the mammal a therapeutically effective amount of the phospholipase $A_2$ inhibitor of claim 6.

25. A method of treating inflammatory and/or allergic conditions mediated by phospholipase $A_2$ in a mammal, comprising administering to the mammal a therapeutically effective amount of the phospholipase $A_2$ inhibitor of claim 7.

26. A method of treating inflammatory and/or allergic conditions mediated by phospholipase $A_2$ in a mammal, comprising administering to the mammal a therapeutically effective amount of the phospholipase $A_2$ inhibitor of claim 8.

27. A method of treating inflammatory and/or allergic conditions mediated by phospholipase $A_2$ in a mammal, comprising administering to the mammal a therapeutically effective amount of the phospholipase $A_2$ inhibitor of claim 9.

28. A pharmaceutical composition of claim 10 which is formulated for topical administration.

29. A pharmaceutical composition of claim 11 which is formulated for topical administration.

30. A pharmaceutical composition of claim 12 which is formulated for topical administration.

31. A pharmaceutical composition of claim 28 wherein the substituted benzylalcohol phospholipase $A_2$ inhibitor is α-(2-([1,4a-dimethyl-7-(2-propyl)-1,2,3,4,4a,9,10,10a-octahydro-1-phenanthren-1-yl]methylamino)ethyl)-4-fluorobenzenemethanol, or a pharmaceutically acceptable salt thereof.

32. A pharmaceutical composition of claim 28 wherein the substituted benzylalcohol phospholipase $A_2$ inhibitor is α-(3-([1,4a-dimethyl-1,2,3,4,4a,9,10,10a-octahydro-7-(2-propyl)-1-phenanthrenyl]methylamino)propyl)-4-fluorobenzenemethanol, or a pharmaceutically acceptable salt thereof.

* * * * *